US00PP20678P2

(12) United States Plant Patent
Hanes

(10) Patent No.: US PP20,678 P2
(45) Date of Patent: Jan. 26, 2010

(54) ***PELARGONIUM* PLANT NAMED 'CANTE PINKA'**

(50) Latin Name: *Pelargonium interspecific*
Varietal Denomination: Cante Pinka

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,986

(22) Filed: Nov. 14, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Annette H Para
(74) *Attorney, Agent, or Firm*—S. Matthew Edwards

(57) ABSTRACT

A new *Pelargonium* plant named 'Cante Pinka,' particularly distinguished by the red-purple color, semi-upright, outwardly spreading and mounding habit, dense and freely basal branching habit, dark green foliage, heat tolerance, and good edema resistance.

1 Drawing Sheet

Latin name of the genus and species of the plant claimed: *Pelargonium interspecific.*

Varietal denomination: 'Cante Pinka'.

BACKGROUND OF THE NEW PLANT

The present invention comprises a new *Pelargonium* hybrid, botanically known as *Pelargonium interspecific*, more specifically as *Pelargonium hortorum* times *Pelargonium tongaense*, hereinafter referred to by the variety name 'Cante Pinka.'

'Cante Pinka' is a product of a planned breeding program. The new cultivar 'Cante Pinka' has red-purple color, semi-upright, outwardly spreading and mounding habit, dense and freely basal branching habit, dark green foliage, heat tolerance, and good edema resistance.

'Cante Pinka' originated from a hybridization in a controlled breeding program in Gilroy, Calif. USA. The female parent was an unpatented *Pelargonium interspecific* hybrid seedling identified as '9994-1' with coral color. '9994-1' has darker foliage, leggy habit, few flowers, and less vigor than 'Cante Pinka.'

The male parent 'Cante Pinka' was an unpatented *Pelargonium interspecific* hybrid seedling identified as '9903-2' with pink color. '9903-2' has a lighter pink color, darker foliage, and less vigor than 'Cante Pinka.'

'Cante Pinka' was selected as one flowering plant within the progeny of the stated cross in October 2005 in a controlled environment in Gilroy, Calif. USA. The pollination was made in February 2005 and the seed sowing in August 2005.

The first act of asexual reproduction of 'Cante Pinka' was accomplished when vegetative cuttings were taken from the initial selection in the October 2005 in a controlled environment in Gilroy, Calif. USA.

Horticultural examination of plants grown from cuttings of the plant initiated in October 2005 in Gilroy, Calif. USA, and continuing thereafter, has demonstrated that the combination of characteristics as herein disclosed for 'Cante Pinka' are firmly fixed and are retained through successive generations of asexual reproduction.

'Cante Pinka' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cante Pinka' has not been made publicly available more than one year prior to the filing of this application.

DESCRIPTION OF THE DRAWINGS

The accompanying photographic drawing shows typical flower and foliage characteristics of 'Cante Pinka' with colors being as true as possible with an illustration of this type. The photographic drawing shows three flowering potted plants of the new variety in a hanging basket and a close-up of the flowers. All were grown and photographed in Gilroy, Calif. USA in July 2008 and were about 3–4 months old.

DETAILED BOTANICAL DESCRIPTION

The measurements were taken in Gilroy, Calif. USA, in October 2008 on plants that were growing in 8 inch plastic pots in a greenhouse. Culture of these plants started in about August 2008 and the plants were about 2 months old.

Color Chart used: Royal Horticultural Society Colour Chart (R.H.S.) 2001.

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY 'CANTE PINKA' AND A SIMILAR VARIETY

| | 'Cante Pinka' | 'Cante Ros' (U.S. Plant Pat. No. 15,834) |
|---|---|---|
| Flower color | Lighter red-purple | Deeper red-purple |
| Petiole size | Shorter | Longer |
| Peduncle size | Shorter | Longer |
| Foliage size | Smaller leaves | Larger leaves |

Plant:

*Form, growth and habit.*—Semi-upright, outwardly spreading and mounding habit, dense habit, freely basal branching habit.

*Plant height.*—8–10 cm.

*Plant height (inflorescence included).*—12–15 cm.

*Plant width.*—20–22 cm.

Foliage:

*Arrangement.*—Alternate.

*Immature, leaf color, upper surface.*—RHS 146A.

*Lower surface.*—RHS 147B.

*Mature, leaf color, upper surface.*—RHS 147A.

*Lower surface.*—RHS 147B.

*Length.*—5.0–5.2 cm.

*Width.*—5.6–5.7 cm.

*Shape.*—Orbicular.

*Base shape.*—Reniform.

*Apex shape.*—Mucronulate.

*Margin.*—Crenate.

*Texture.*—Hirsute.

*Color of zone.*—Very slight hue of RHS N200A.

*Width of zone.*—0.5 cm.

*Color of veins, upper surface.*—Indistinct.

*Color of veins, lower surface.*—Slightly lighter than RHS 147B.

*Petioles color.*—RHS 146A.

*Petioles length.*—4.3–4.5 cm.

*Diameter of petiole.*—0.2 cm.

*Texture.*—Hirsute; pilose.

Stem:

*Color of stem.*—RHS 146A; anthocyanins of about slightly close to RHS 166A basally.

*Length of stem.*—11–13 cm.

*Diameter.*—0.4 cm.

*Length of internodes.*—1–2 cm.

*Texture.*—Hirsute.

Inflorescence:

*Type.*—An umbel composed of 13–16 flowers and buds.

*Color of peduncle.*—RHS 146B with anthocyanin overlay of about RHS N199A.

*Length of peduncle.*—8.5–8.7 cm.

*Peduncle diameter.*—0.2–0.3 cm.

*Texture.*—Hirsute; pilose.

*Color of pedicel.*—RHS 187A.

*Length of pedicel.*—3.5–3.6 cm.

*Diameter of pedicel.*—0.1–0.15 cm.

*Texture.*—Hirsute.

*Umbel diameter.*—11.5–11.9 cm.

*Umbel depth.*—6.5–6.8 cm.

*Number of umbels per plant.*—2.

*Duration of flowering.*—Continuous flowering throughout the summer.

*Lastingness of flowers.*—About 1 week.

Corolla:

*Form.*—Single; polypetalous, composed of 5 petals, lower petals do not overlap.

*Length of flower.*—3.5–4.0 cm.

*Width of flower.*—3.9–4.5 cm.

*Color upper petals, upper surface.*—RHS 68A base color; RHS N155B but whiter basal blotch with RHS 64B in the veins.

*Color upper petals, lower surface.*—RHS 73A; lighter basally.

*Length of upper petals.*—2.3–2.5 cm.

*Width of upper petals.*—1.3–1.5 cm.

*Color lower petals, upper surface.*—RHS 68A.

*Color lower petals, lower surface.*—RHS 73A.

*Length of lower petals.*—2.5–2.6 cm.

*Width of lower petals.*—1.7–1.8 cm.

*Petal shape.*—Slightly spathulate to obovate.

*Apex shape.*—Rounded.

*Margin.*—Entire.

*Petal texture.*—Papillose on both surfaces.

Bud (just before opening):

*Color.*—RHS 58A on the upper facing side; RHS 58C on the under facing side.

*Length.*—1.1–1.2 cm.

*Width.*—0.5 cm.

*Shape.*—Ovate.

Calyx:

*Number of sepals.*—5.

*Color of sepals.*—RHS 187A.

*Length of sepals.*—1.0–1.1 cm.

*Width of sepals.*—0.3–0.35 cm.

*Sepal shape.*—Lanceolate.

*Apex shape.*—Acute.

*Margins.*—Entire.

*Texture.*—Hirsute; pilose.

Reproductive organs:

*Pistil.*—1.

*Length.*—0.4 cm.

*Style color.*—RHS 71B.

*Style length.*—0.2 cm.

*Stigma color.*—RHS 71B.

*Number of stamens.*—4–6.

*Color of filaments.*—RHS N155B but whiter basally; RHS 72B at the anther.

*Length filaments.*—0.3–0.4 cm.

*Anther color.*—RHS 71C.

*Color of pollen.*—RHS 26A.

*Pollen amount.*—Moderate.

*Fertility/seed set.*—Not observed on this hybrid.

Disease/pest resistance: Disease resistance or susceptibility has not been observed on this hybrid.

What is claimed is:

1. A new and distinct variety of *Pelargonium* plant named 'Cante Pinka,' substantially as illustrated and described herein.

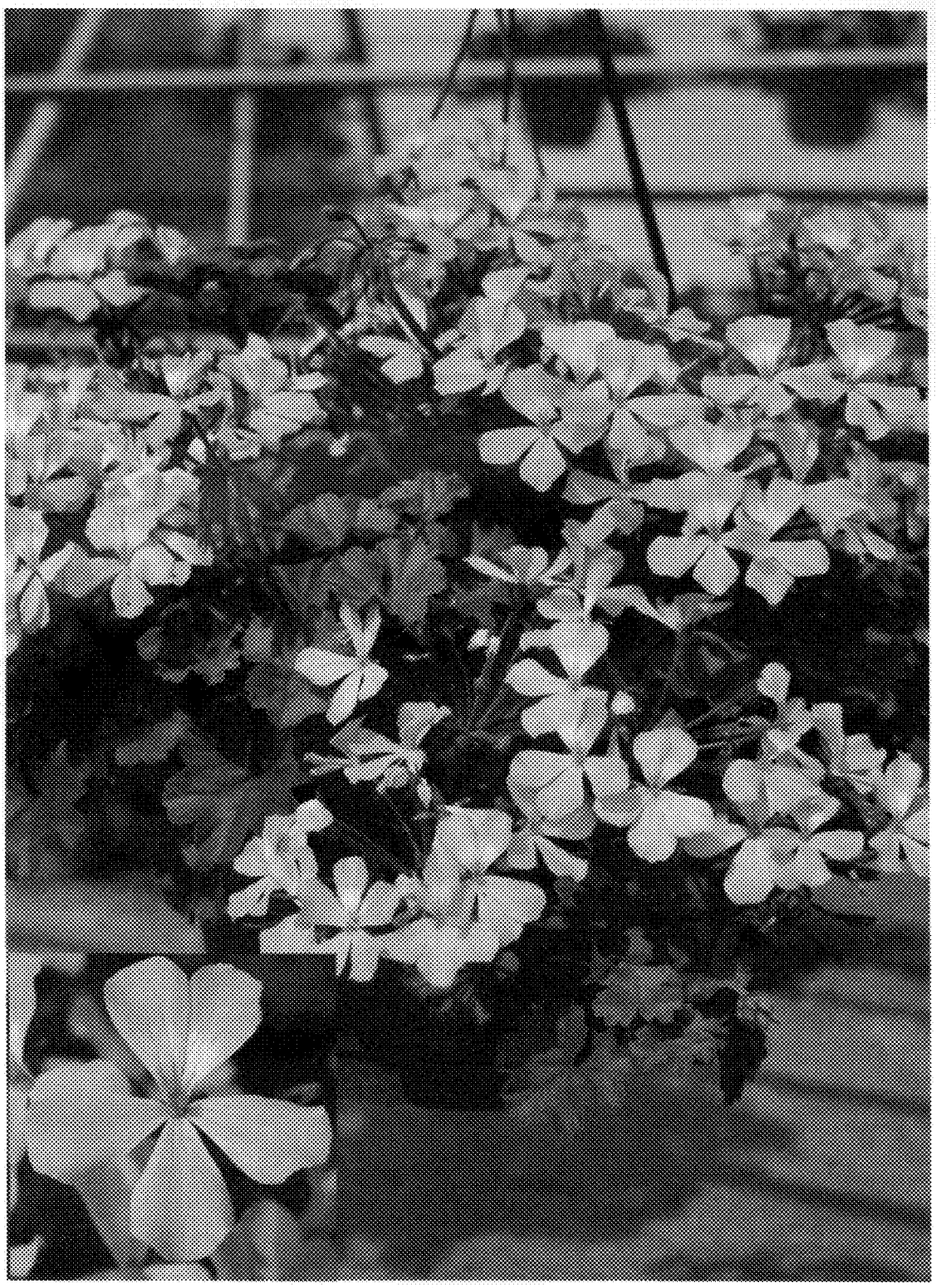

* * * * *